United States Patent [19]

Farolfi et al.

[11] Patent Number: 5,085,867
[45] Date of Patent: Feb. 4, 1992

[54] METHOD FOR TREATING GASTRIC ULCER WITH SULGLYCOTIDE AND HYDROPHILIC POLYMER

[75] Inventors: Giancarlo Farolfi; Giovanni Gazzani, both of Como; Riccardo Niada, Varese; Marisa Mantovani, Villa Guardia, all of

[73] Assignee: Crinos Industria Farmacobiologica SpA, Villa Guardia, Italy

[21] Appl. No.: 501,698

[22] Filed: Mar. 30, 1990

Related U.S. Application Data

[62] Division of Ser. No. 138,400, Dec. 18, 1987, Pat. No. 4,937,079.

[30] Foreign Application Priority Data

Jan. 12, 1987 [IT] Italy .............................. 19048 A/87

[51] Int. Cl.⁵ .......................... A61K 9/14; A61K 9/20; A61K 37/02; A61K 47/38

[52] U.S. Cl. .................................. 424/485; 424/488; 424/499; 424/500; 424/501; 424/464; 514/8
[58] Field of Search ...................... 424/485, 78; 514/8

[56] References Cited

U.S. PATENT DOCUMENTS

| | | | |
|---|---|---|---|
| 3,926,921 | 12/1975 | Butti et al. | 514/8 |
| 3,961,045 | 6/1976 | Wurzburg et al. | 428/78 |
| 4,151,276 | 4/1979 | Caulin et al. | 530/307 |
| 4,937,079 | 6/1990 | Farolfi et al. | 424/480 |

Primary Examiner—Thurman K. Page
Assistant Examiner—E. J. Webman
Attorney, Agent, or Firm—Armstrong, Nikaido, Marmelstein, Kubovcik & Murray

[57] ABSTRACT

The oral administration to an animal of sulglycotide '(a sulfoglycopeptide)' together with methylcellulose, pectin or tragacanth gum protects the animal against gastric ulcer.

4 Claims, No Drawings

METHOD FOR TREATING GASTRIC ULCER WITH SULGLYCOTIDE AND HYDROPHILIC POLYMER

This is a division of application Ser. No. 138,400 filed Dec. 28, 1987, which issued as U.S. Pat. No. 4,937,079 on June 26, 1990.

The present invention relates to a pharmaceutical composition useful for the prophylaxis and therapy of gastric ulcer.

The importance of gastric ulcer as a therapeutic problem does not require: it is enough to remember that in the last 10 years important drugs have been invented and developed, such as cimetidine and ranitidine, having this main activity.

Parallel to the development of new drugs, a huge research effort has been dedicated to the investigation of the causes and of the mechanisms involved in this pathology.

These researches, of essentially pharmacological character, are based on experiments in which the activity of the drug is evaluated with respect to the effectiveness shown in preventing the occurrence of an experimentally induced ulcer.

A number of these studies has been recently aimed at the evaluation of drugs now in use in such a pathology in order to assess whether they would be capable of protecting the gastric mucosae, in the presence of necrotizing agents, in an experimental model in which the gastric acid secretion would remain unchanged. This experimental model has been suggested by Robert (A. Robert et al. "Cytoprotection by prostaglandins in rats" Gastroenterol. 77, 443–443, 1979) in order to demonstrate that prostaglandins were active in protecting the gastric mucosae from lesions or necrosis, localized in the secreting portion of the stomach, as induced by several substances, (absolute ethanol, 0.2 N NaOH, 0.6 N HCl, 25% NaCl, boiling water).

This effect, however, was not related to the inhibition of acid secretion; in fact anticholinergic drugs (methscopolamine bromide) or anti-$H_2$ drugs (cimetidine) or even anti-acidic drugs (sodium bicarbonate), if administered alone were not active in preventing lesions. These unexpected results stimulated studies designed to assess the effectiveness in the same tests of other drugs used in this pathology, also in order to clarify possible connections to mediating substances (the prostaglandins) supposedly involved in such a mechanism of defence of the gastric mucosae.

It has been demonstrated that after only one dose of both ranitidine (A. Tarnasky, "Comparison of antacid, sucralfate, cimetidine and ranididine in protection of astric mucosa ethanol injury" Gastroenterology 84, 1331 1983) and atropine (J. Puurunen et al., "Effect of prostaglandin E2, cimetidine and atropine on ethanol induced mucosal damage in the rat," Scand. J. Gastroenterol. 15, 484–488 1950) are not active. To the contrary sucralfate (A. Tarnawsky, same above cited paper), carbenoxolone (BY. C. Wan, "Cytoprotective action of carbenoxolone sodium on ethanol-induced gastric lesions in rats and its inhibition by indomethacin", J. Pharm. Pharmacol., 37, 739–741, 1985) and under some aspects also piranzepine (E. Trabucchi et al. "Cytoprotection by PGE2, piranzepine or vagotomy; a transmission and scanning microscope electron microscope study in rats," Pharm. Res. Comm., 18, 357-369, 1986) are active.

The results of these subsequent experiments confirmed the observations of Robert as regards the lack of activity in such a test anti-$H_2$ anti-acid and anti-cholinergic products.

These data are not in conflict with the proved pharmacological and clinical efficacy of these drugs. More simply, the Robert's test does not foresee that acidic gastric secretion is the factor inducing the ulcer, as it occurs in other tests, such as for instance the Shay ulcer.

The subject experimental model does reveal the activity of those drugs acting through a different mechanism in ulcer pathology, namely by enhancing the endogenic mechanisms of protection of the gastric mucosa, such as carbenoxolone and sucralfate, the clinical activity of which in the ulcer therapy has been widely evidenced and acknowledged. It is noted that the latter approach to this therapeutical problem is relevant with respect to the possibility of preventing ulcer formation, which normally is the subsequent and final step of the pathology known as "non ulceric dyspepsia".

As it is known from medical science, non ulceric dyspepsia has the same symptomatology as true ulcer, from which it can be however distinguished through the stomach exploration by endoscopic route.

In this case anti-$H_2$ and anti-acid drugs have been in fact found devoid of efficacy (P. Lance et Al., "A controlled clinical trial of cimetidine for the treatment of non-ulcer dyspepsia" J. Clin. Gastroent., 8, 414–8, 1986; J. M. B. Saunders et Al., "Dyspepsia: incidence of non-ulcer disease in a controlled trial of ranitidine in general practice" Brit. Med. J., 292, 665-9, 1986; O. Nyren et Al. "Absence of therapeutic benefits from antacids or cimetidine in non-ulcer dyspepsia" New England J. Med., 314, 6, 339-343, 1986; Editorial Notes in the Lancet. 1306–7, 1986).

These results, very probably, are to be related to the fact that most of the subjects, which later on are involved in true ulceric pathology, have a normal gastric secreting activity, whereas only a minor part can be properly defined as "hypersecretors" (J. P. Horrocks et al., "Clinical presentation of patients with dyspepsia. Detailed Sympotomatic study of 360 patients" Gut, 19, 19–26, 1978; K. M. Mollman et Al., "A diagnostic study of patients with upper abdominal pain" Scand. J. Gastroenterol., 10, 805–9, 1975).

Sulglycotide (D.C.I. OMS liste No. 13, Chronique OMS 27-10 1973) is a macromolecule obtained through direct sulfonation of a glycopeptide extracted from the gastric or duodenal mucosa of swine (U.K. Patent 1,249,907) and has been used for several years in the prophylaxis and therapy of gastric and duodeneal ulcer.

This drug, already tested several years ago with success in a number of models of experimental ulcer (G. Prino et Al., "Inhibition of experimentally induced gastric ulcers in the rat by a new sulfated glycopeptide", Eur. J. Pharmacol., 15, 119–126, 1971), did not show satisfactory activity in the Robert's model (R. Niada et al. "Cytoprotection by sulglycotide; prevention of gastric necrosis in rat" "Pharm. Res. Comm., 13, 695–704, 1981).

It has not been possible to demonstrate a protecting activity for sulglycotide towards gastric mucosa having the same efficacy as carbenoxolone or sucralfate; in fact, whereas the activity of these two drugs was evident after only one administration, for the sulglycotide five administrations were necessary, repeated every 24 hours from each other. The doses were of between 25 and 200 mg/kg.

More particularly, according to these results, it was not to be expected that sulglycotide, might be useful in non ulceric dyspepsia as previously discussed as regards the causes and the rationale on which the therapy is based.

Among the pharmaceutical forms the oral ones are the most widely used because they are easy to carry and take and have a pleasant taste. Moreover they are evidently advantageous for the manufacturer owing to their easy and economic preparation.

For these formulations the use of hydrophilic polymers is known as density enhancers and to prepare suitable suspensions of compounds not soluble in aqueous medium, or as stabilizers for the emulsions.

These substances can be used as binders and as disgregating agents in the preparation of tablets (for examples, polyvinylpyrrolidone, sodium carboxymethylcellulose).

According to Remington's Pharmaceutical Sciences 16th Ed., 1980 (Mack Publishing Company) hydrophilic polymers can be grouped in three basic classes:
- natural polymers, such as for instance locust gum, agar-agar, guar gum, pectin, sodium alginate, xantan gum, carrageenin;
- cellulose derivatives such as for example methyl cellulose, hydroxy ethyl cellulose, hydroxy propyl cellulose;
- synthetic polymers such as for example polyvinylpyrrolidone.

Among these substances pectin is used in the treatment of diarrhea in children owing to its properties as an intestinal absorber.

It has been now surprisingly found and is the subject of the present invention that by combining sulglycotide with at least one the above mentioned polymers the anti-ulcer activity of the drug is enhanced according to the test of Robert, and consequently the sulglycotide in this type of combination and composition shows a significant gastroprocting effect even after only one administration.

The data reported in table I have been obtained by inducing ulcer through the administration of ethanol (1 ml) to the rat three hours after the single administration per os at the doses, relating to the tested substances, which are reported in the same table.

The animals were sacrificed 5 hours after ethanol administration. The stomach was then removed and was opened at the big bend.

The mucosa was then examined and a score was given to the necrotic lesions depending on their heaviness.

TABLE I

Ethanol induced ulcer effects of some hydrophilic polymers and of the sulglycotide, administered only one time three hours before the ethanol. Average value ± Standard Error of 16 data per group.

| Substance | Dose mg/kg p.o. | Gastric lesions (score) | Protection % vs H$_2$O |
|---|---|---|---|
| H$_2$O | 10 ml/kg | 4.12 ± 0.31 | — |
| methylcellulose | 185 | 3.78 ± 0.26 | 8.25* |
| pectin | 340 | 3.87 ± 0.26 | 6.07* |
| thragacant gum | 300 | 3.84 ± 0.26 | 6.80 |
| H$_2$O | 10 ml/kg | 3.94 ± 0.15 | — |
| sulglycotide | 200 | 3.53 ± 0.24 | 10.41* |

*Statistically non significant protection (ANOVA, Tukey Test).

The particular hydrophilic polymers to which reference is made in this table and in the following one are to be meant as reported only for example and in a non-limiting sense as regards the substances belonging to this class which can be used for the purposes to be attained with the present invention.

Table II illustrates the results obtained in the same test by using the corresponding mixtures, (referred to in the following formulation examples) with sulglycotide and the hydrophilic polymers of the table I, and at the same doses reported herein.

TABLE II

Ethanol induced ulcer protecting effects of the sulglycotide combined with several hydrophilic polymers, administered only one time three hours before ethanol. Average values ± Standard Error of 20 data for group.

| Substance | Dose mg/kg p.o. | Gastric lesions (score) | Protection % vs H$_2$O |
|---|---|---|---|
| H$_2$O | 10 ml/kg | 4.60 ± 0.17 | — |
| sulglycotide (A) + methylcellulose (B) | A = 200 B = 185 | 3.15 ± 0.31* | 31.52 |
| sulglycotide (A) + pectin (B) | A = 200 B = 340 | 2.27 ± 0.24* | 50.65 |
| sulglycotide (A) + thragacant gum (B) | A = 200 B = 300 | 3.02 ± 0.31* | 34.35 |

*P <0.01 (ANOVA, Tukey test)

It has been moreover assessed that the sulglycotide in such a combination shows in the Robert's test an activity which is proportional to the administered dose.

A gel pharmaceutical form containing increasing amounts of sulglycotide according to the formulations described in examples 1A-1C, has been tested against the corresponding placebo and against sulglycotide along (400 mg/kg dose) in the ethanol induced ulcer test and in the NaOH induced ulcer test.

The gel volumes were 10 ml/kg. In the case of the NaOH induced ulcer the formulations according to examples 1A-1C were diluted in the ratio 1:1 before the experiment.

TABLE III

Ethanol induced ulcer-effects of sulglycotide in gel administered only one time at different doses (formulations 1A-1C) 3 hours before ethanol. Under the same experimental conditions, sulglycotide alone and the placebo were tested. Average values ± Standard Error of 18 data per group.

| Substance | Dose mg/kg p.o. | Gastric lesions (score) | Protection % vs H$_2$O |
|---|---|---|---|
| distilled H$_2$O | 10 ml/kg | 3.94 ± 0.15 | — |
| placebo gel | 10 ml/kg | 3.53 ± 0.18 | 10.41 |
| sulglycotide gel (ex. 1A) | 100 | 3.06 ± 0.29 | 22.23 |
| sulglycotide gel (ex. 1B) | 200 | 2.17 ± 0.32* | 44.92 |
| sulglycotide gel (ex. 1C) | 400 | 1.25 ± 0.30§ | 68.27 |
| sulglycotide in H$_2$O | 400 | 3.53 ± 0.24 | 10.41 |

*P <0.01 (Anova Tukey test)

The calculated ED$_{50}$ was 403.09 (299.05-507.13) mg/kg p.o.

TABLE IV

NaOH induced ulcer - effects of sulglycotide in gel administered only one time at different doses (formulations 1A-1C) three hours before NaOH. Under the same experimental conditions, sulglycotide alone and placebo were also tested. Average values ± Standard Error 18 data per group.

| Substance | Dose mg/kg p.o. | Gastric lesions (score) | Protection % vs H$_2$O |
|---|---|---|---|
| distilled H$_2$O | 10 ml/kg | 3.73 ± 0.21 | |
| placebo gel | 10 ml/kg | 3.26 ± 0.31 | 12.60 |
| sulglycotide gel (ex. 1A) | 50 | 2.40 ± 0.32 | 35.66 |
| sulglycotide gel (ex. 1B) | 100 | 1.13 ± 0.16* | 69.70 |

TABLE IV-continued

NaOH induced ulcer - effects of sulglycotide in gel administered only one time at different doses (formulations 1A-1C) three hours before NaOH. Under the same experimental conditions, sulglycotide alone and placebo were also tested. Average values ± Standard Error 18 data per group.

| Substance | Dose mg/kg p.o. | Gastric lesions (score) | Protection % vs $H_2O$ |
|---|---|---|---|
| sulglycotide gel (ex. 1C) | 200 | 0.70 ± 0.19* | 81.22 |
| sulglycotide in $H_2O$ | 400 | 3.73 ± 0.27 | 0 |

*P <0.01 (Anova Tukey test)

The calculated $ED_{50}$ was 40.5 (31.2-52.4) mg/kg p.o.

As it is evident from the tables III and IV, the activity of sulglycotide in both experimental conditions is highly significant and depending on the dose if the substance is combined with hydrophilic polymers.

In both cases, in fact, it has been possible to calculate the corresponding value of $ED_{50}$.

Sulglycotide along, even at the dose of 400 mg/kg, is devoid of activity.

Lastly it has been assessed whether in the test under consideration the hydrophilic polymers were able to act in the same sense on the activity of other gastroprotecting drugs.

As an example, sucralfate has been selected, which has been tested in the rat both alone and in admixture with pectin.

The results obtained are reported in the table V. The experimental scheme was the same of the ethanol induced ulcer and the administered volume was 10 ml/kg.

TABLE V

Ethanol induced ulcer - effect of sucralfate and pectin, sucralfate alone and pectin alone administered only one time before the ethanol. Average ± Standard Error of 20 data per group (16 data for the sucralfate alone).

| Substance | Dose mg/kg p.o. | Gastric lesions (score) | Protection % vs $H_2O$ |
|---|---|---|---|
| $H_2O$ | 10/ml/kg | 4.55 ± 0.14 | — |
| pectin | 340 | 4.30 ± 0.21 | 5.49 |
| sucralfate (A) + pectin (B) | A = 200 B = 340 | 4.05 ± 0.23 | 10.99 |
| sucralfate in $H_2O$ | 200 | 0.69 ± 0.20* | 84.83 |

*P <0.01 (ANOVA, Tukey test).

From table V it is evident that by adding a hydrophilic polymer (pectin to the sucralfate) not only the drug activity does not increase but on the contrary is significantly reduced. This fact is further evidence of the uniqueness of the interaction between the sulglycotide and said polymers which very probably is related to the fact that both these substances are macromolecules.

Example of formulation for oral use according to the present invention are now reported.

The pharmaceutical composition for oral use according to the present invention can be prepared in form of tablets and granulates for single dose packages in small envelopes or in form of gels or emulsions.

The daily average of the compositions of the invention is of between 200 and 600 mg based on the amount of sulglycotide.

As regards the pharmaceutical forms in tablets or granulates, the respective amounts of sulglycotide and of hydrophilic polymer may very between 50 and 500 mg.

In the gel the same amounts may vary between 1% and 5% by weight. The ratio between sulglycotide and hydrophilic polymer may very between 1:1 and 1:5.

EXAMPLE 1: Gel (% Composition)

|  | A | B | C |
|---|---|---|---|
| sulglycotide | 1 | 2 | 4 |
| pectin | 3.6 | 3.6 | 3.6 |
| propylene glycol | 4 | 4 | 4 |
| excipients | 20.92 | 20.92 | 20.92 |
| preservants | 0.15 | 0.15 | 0.15 |
| $H_2O$ enough to | 100 | 100 | 100 |

EXAMPLE 2: Emulsion (% Composition)

|  | A | B | C |
|---|---|---|---|
| sulglycotide | 1 | 2 | 4 |
| guar gum | 5 | 5 | 5 |
| 70% sorbitol | 74 | 73 | 71 |
| mais oil | 20 | 20 | 20 |

EXAMPLE 3: Gel (% Composition)

| sulglycotide | 2 |
|---|---|
| hydroxypropylmethylcellulose | 4 |
| 70% sorbitol | 15 |
| preservants | 0.15 |
| $H_2$ enough to | 100 |

EXAMPLE 4: Gel (% Composition)

| sulglycotide | 2 |
|---|---|
| methylcellulose | 1.85 |
| 70% sorbitol | 15 |
| preservants | 0.15 |
| $H_2O$ enough to | 100 |

EXAMPLE 5: Gel (% Composition)

| sulglycotide | 2 |
|---|---|
| carrageenin | 1.77 |
| preservants | 0.15 |
| 70% sorbitol | 15 |
| $H_2O$ enough to | 100 |

EXAMPLE 6: Gel (% Composition)

| sulglycotide | 2 |
|---|---|
| thragacant gum | 3 |
| 70% sorbitol | 15 |
| preservants | 0.15 |
| $H_2O$ enough to | 100 |

EXAMPLE 7: Gel (% Composition)

| sulglycotide | 2 |
|---|---|
| pectin | 3.40 |
| excipients | 11.22 |
| preservants | 0.15 |
| $H_2O$ enough to | 100 |

EXAMPLE 8: Masticable or to be Sucked Tablets (Composition in mg)

|  | A | B |
|---|---|---|
| sulglycotide | 100 | 200 |
| pectin | 200 | 200 |
| standard excipients enough to | 2000 | 2000 |

EXAMPLE 9: Granulates for Extemporaneous Gel (Composition in mg)

|  | A | B | C |
|---|---|---|---|
| sulglycotide | 100 | 200 | 400 |
| pectin | 360 | 360 | 360 |
| preservants | 14.4 | 14.4 | 14.4 |
| standard excipients enough to | 3600 | 3600 | 3600 |

We claim:

1. A method for protecting an animal against gastric ulcer which comprise orally administering to the animal a gastroprotective amount of sulglycotide together with a hydrophilic polymer selected from the group consisting of methylcellulose pectin and tragacanth gum, such that the ratio of sulglycotide per part by weight to the hydrophilic polymer per part by weight is between 1:2 and 1:5.

2. A method according to claim 1, wherein the sulglycotide together with hydrophilic polymer are administered in the form of a tablet, granulate or gel.

3. A method according to claim 2, wherein the tablet or granulate contains between 50 and 500 mg each of the sulglycotide and the hydrophilic polymer.

4. A method according to claim 2, wherein the gel contains between 1 and 5% by weight each of the sulglycotide and the hydrophilic polymer.

* * * * *

UNITED STATES PATENT AND TRADEMARK OFFICE
CERTIFICATE OF CORRECTION

PATENT NO. : 5,085,867
DATED : February 4, 1992
INVENTOR(S) : Giancario Farolfi, ET AL It is certified that error appears in the above-identified patent and that said Letters Patent is hereby corrected as shown below:

On the cover page, Item [75], after "all of " insert --Italy--.
Item [62], delete "18" and substitute therefor -- 28 --.

Signed and Sealed this

Twenty-second Day of June, 1993

Attest:

MICHAEL K. KIRK

*Attesting Officer*   Acting Commissioner of Patents and Trademarks